(12) United States Patent
Berger et al.

(10) Patent No.: US 7,863,476 B1
(45) Date of Patent: Jan. 4, 2011

(54) MULTIFUNCTIONAL ANIONIC SURFACTANTS

(75) Inventors: Paul Daniel Berger, Sugar Land, TX (US); Christie Huimin Berger, Sugar Land, TX (US)

(73) Assignee: Oil Chem Technologies, Sugar Land, TX (US)

( * ) Notice: Subject to any disclaimer, the term of this patent is extended or adjusted under 35 U.S.C. 154(b) by 0 days.

(21) Appl. No.: 12/592,318

(22) Filed: Nov. 23, 2009

(51) Int. Cl.
*C07C 303/00* (2006.01)
*C07C 307/00* (2006.01)
*C07C 309/00* (2006.01)
*C07C 311/00* (2006.01)

(52) U.S. Cl. .................................................. 560/14
(58) Field of Classification Search .................... 560/14
See application file for complete search history.

(56) References Cited

U.S. PATENT DOCUMENTS

| | | |
|---|---|---|
| 3,575,883 A | 4/1971 | Foley |
| 4,458,759 A | 7/1984 | Isaacs et al. |
| 6,022,834 A | 2/2000 | Hsu et al. |
| 6,043,391 A | 3/2000 | Berger et al. |
| 2009/0023951 A1 | 1/2009 | Berger et al. |

*Primary Examiner*—Daniel M Sullivan
*Assistant Examiner*—Jennifer C Sawyer

(57) ABSTRACT

This invention describes a composition of matter of the following structure:

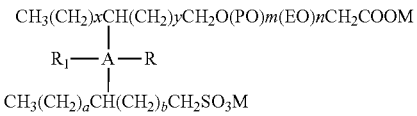

where $m+n=1-30$ or more,
$x+y=0-28$,
EO=oxirane
PO=methyl oxirane
M=H, Na, K, $NH_3$, Amine, Ca, Mg,
R and R1 are each separately and independently H, branched or linear alkyl, branched or linear alkenyl,
A=aromatic, and,
$a+b=0$ to 30.

2 Claims, No Drawings

MULTIFUNCTIONAL ANIONIC SURFACTANTS

CROSS REFERENCE TO RELATED APPLICATIONS

None

STATEMENT REGARDING FEDERALLY SPONSORED RESEARCH OR DEVELOPMENT

Not Applicable

DESCRIPTION OF ATTACHED APPENDIX

Not Applicable

BACKGROUND OF THE INVENTION

The present invention relates to a composition of matter containing both ether carboxylate and sulfonate groups on the same molecule. The unique properties of the composition makes it suitable for many surfactant applications including but not limited to enhanced oil recovery (EOR), detergents, metal treating, agricultural formulations, mining, de-inking, paper processing, textile processing, coatings, adhesives, lubricants.

In the recovery of oil from subterranean reservoirs it usually is possible to recover approximately 15%-20% of the original oil in place by primary recovery. Secondary recovery methods such as well stimulation or water flooding are applied after the amount of oil recovered by primary recovery becomes uneconomical. Secondary recovery methods can recover approximately an additional 15%-30% of the original oil in place which leaves the reminder of the oil unrecoverable unless other means such as tertiary recovery processes are applied. These tertiary recovery methods include but are not limited to the use of miscible and immiscible gases and liquids, steam, foam, alkali, surfactants, and polymers.

It has been known that many factors including but not limited to the interfacial tension between the injection brine and the residual oil, the relative mobility of the injected brine, and the wettability characteristics of the rock surfaces comprising the reservoir are all important in determining the amount of oil recovered by tertiary recovery. Numerous studies have found that the addition of surfactants to the injection brine can alter the interfacial and wetting properties to help overcome the high capillary pressure and increase the oil recovery. In many cases the addition of a polymer along with the surfactant or immediately after the surfactant can increase the mobility ratio between the injected brine and oil thus further improving the sweep efficiency of the flood.

Because the injection brine composition varies, it is important to use the brine available at the injection site for the tertiary process in order to be economically feasible. It is important to have surfactants that are compatible with brines having wide ranges of total dissolved solids (TDS) and divalent cations such as those of calcium and magnesium. The problem with many of the presently used surfactants in tertiary oil recovery is that they are incompatible with the brines containing high TDS and divalent cations that are often found at the injection site. Costly water treatment processes or using an alternate fresh water source makes the tertiary recovery process economically unfeasible in many cases. Therefore it is important to have surfactants that are tolerant to the high TDS and divalent cations. It is also important that the surfactant be tolerant to the high temperatures encountered in some wells and to show limited adsorption on to the reservoir rock. Most surfactants cannot meet all these requirements and in many cases blends of several different types of surfactants are used to meet the specific requirements. When blends are used a strong possible of chromatographic separation exist as the surfactant blend propagates through the reservoir due to differential adsorption properties.

Anionic surfactants, especially sulfonates have been found to be very stable to high temperatures however they are not tolerant to brines of high salinities especially those containing small amounts of divalent cations. Ether carboxylates are very tolerant to high temperatures and high salinities but they fail to give the required low interfacial tensions required to recover oil. We have found a method of producing surfactants having both the properties of ether carboxylates and sulfonates on the same molecule enabling the recovery of oil from reservoirs having a wide range of salinities, hardness and temperatures.

Many examples of using mixtures of two or more surfactants to lower interfacial tension and recover residual oil can be found in the literature. U.S. Pat. No. 6,022,834 issued to Hsu et al discloses the use of mixtures of carboxylated anionic surfactants with sulfonated surfactants. U.S. Pat. No. 4,458,759 issued to Issacs teaches a composition comprising organic sulfonate surfactants such as sulfonate fatty acids having both weak and strong anionic functionality groups. These products are derived from fatty acids and as such cannot form stable ethers when reacted with ethylene or propylene oxides and therefore do not exhibit the thermal stability of the compounds described in the present invention. Processes and surfactants have been described in the literature using sulfonated oleic acid, for example, U.S. Pat. No. 3,575,883 to Foley. Besides being derived from acids to give unstable esters when alkoxylated, these employ conventional means of sulfonation and are limited to lower molecular weight products because of reduced sulfonation efficiency with high molecular weight products. The products of the present invention use a different sulfonation procedure and are not limited to low molecular weight products. Therefore highly alkoxylated products of molecular weights exceeding 1000 can be easily manufactured. The composition of the present invention is an ether carboxylate having an additional sulfonate group on the molecule. The ether carboxylate group has been shown to be very salt tolerant and thermally stable. The sulfonate group provides thermal stability as well as lowering the interfacial tension. The two negative charges on the same molecule help to lower adsorption unto reservoir rock that is usually negatively charged by electrostatic repulsion. This combination of an alkyl ether carboxylate and an alkyl sulfonate attached to an aromatic spacer disclosed in the present invention is unique and provides synergistic performance that has not been anticipated before.

BRIEF SUMMARY OF THE INVENTION

The present invention is directed to the compositions containing surfactants having an ether carboxylate functionality group and a sulfonate functionality group on the same molecule. This composition may be formulated into a concentrated surfactant blend containing an aqueous solvent such as water or brine, and a co-surfactant/solvent such as a lower molecular weight alcohol or alcohol ether for use as an EOR surfactant.

In the present invention, the ether carboxylate group and the sulfonate groups on the same molecule provide several advantages over mixtures of surfactants having each of the functionalities on separate molecules. The single molecule containing the two groups eliminates the possibility of chromatographic separation when subjected to a strong adsorbent such as when injected into an oilfield reservoir.

DETAILED DESCRIPTION OF THE PREFERRED EMBODIMENTS

Detailed descriptions of the preferred embodiment are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure or manner.

Structure I below describes the compound of this invention. This structure shows the aromatic group as A. Single ring structures including but not limited to benzene, toluene, o-xylene, m-xylene, p-xylene, phenol as well as multiple ring structures including but not limited to naphthalenes or phenyl ethers are examples of aromatics that are part of the present invention.

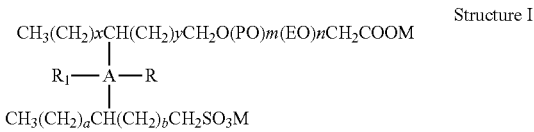

Structure I where m+n=1-30 or more, x+y=0-28,

EO=oxirane

PO=methyl oxirane

M=H, Na, K, $NH_3$, Amine, Ca, Mg,

R and R1 are each separately and independently H, branched or linear alkyl, branched or linear alkenyl, A=aromatic, and, a+b=0 to 30.

The composition of this invention depicted as Structure I is made by reacting an unsaturated ether carboxylate as depicted in Structure II with a sulfonic acid depicted in Structure III using the procedure described in U.S. Pat. No. 6,043,391 and U.S. patent application Ser. No. 11/895,497. Although 11/895,297 describes many derivatives that can be made by reacting Structure II with various unsaturated molecules, it is silent with respect to the reaction of an unsaturated ether carboxylate with structure II.

The composition of this invention is made by reacting Structure II with Structure III at temperatures between 80 and 150° C.

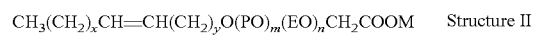
$CH_3(CH_2)_xCH=CH(CH_2)_yO(PO)_m(EO)_nCH_2COOM$    Structure II where m+n=1-30 or more

M=H, x+y=0-27,

Structure III

Where R, $R_1$ are each separate and independently H, branched or linear alkyl, branched or linear alkenyl, $R_2$=H A=aromatic, and, a+b=0 to 30.

EO=oxirane, and

PO=methyl oxirane.

The initial product is made in the acid form where M=H and can then be neutralized with various basic materials including but not limited to sodium hydroxide, sodium carbonate, potassium hydroxide, ammonium hydroxide, calcium hydroxide, magnesium hydroxide, isopropyl amine, The unsaturated carboxylate moiety may contain from about 0 to about 30 or more moles of an alkoxy group such as ethylene oxide (EO), propylene oxide (PO), or mixtures of EO and PO, or sequences of EO and PO, to adjust the solubility and molecular weight of the surfactant. Unsaturated ether carboxylates include but are not limited to oleyl alcohol ether carboxylates, erucyl alcohol ether carboxylates, nervonyl alcohol ether carboxylates.

Table I lists the surfactants used to in the examples chosen to demonstrate the utility and novelty of the invention. In all cases the surfactant formulation consisted of 30% by weight surfactant, 25% by weight ethylene glycol monobutyl ether (co-surfactant/solvent), and 45% by weight water. Also in all cases except where noted the surfactant formulation was added to the injection brine at a concentration of 0.10 weight percent. These examples use surfactants containing only ethylene oxide in the alcohol ether carboxylate although products containing propylene oxide and ethylene oxide give good results in certain applications.

TABLE I

Surfactants Used In Examples

| SURFACTANT | CHEMICAL DESCRIPTION |
|---|---|
| A | Structure I where x = 7, y = 8, m = 0, n = 2, M = Na, and a + b = 11. |
| B | Structure I where x = 7, y = 8, m = 0, n = 9, M = Na, and a + b = 11. |
| C | Sodium salt of carboxylated oleyl alcohol with 2 moles of EO. |
| D | Sodium salt of carboxylated oleyl alcohol with 9 moles of EO. |
| E | Sodium salt of structure II where a + b = 11 |

Table II is the brine compositions that were used for the IFT testing to show the effect of total dissolved solids and divalent ion concentration on the IFT obtained using various surfactants.

TABLE II

Brine Compositions

| BRINE | 1 | 2 | 3 | 4 | 5 |
|---|---|---|---|---|---|
| NaCl, % | 3.0 | 1.0 | 5.0 | 10 | 20 |
| CaCl2-2H2O, % | 1.0 | 0 | 0 | 0 | 0 |
| MgCl2-6H2O, % | 1.0 | 0 | 0 | 0 | 0 |

Table III compares the solubilities obtained with 5.0% by weight of various surfactant concentrates in the 5 brines at 30° C.

TABLE III

Brine Solubilities

| TEST | SURFAC-TANT | BRINE 1 | BRINE 2 | BRINE 3 | BRINE 4 | BRINE 5 |
|---|---|---|---|---|---|---|
| 1 | A | soluble | soluble | soluble | insoluble | insoluble |

TABLE III-continued

Brine Solubilities

| TEST | SURFAC-TANT | BRINE 1 | BRINE 2 | BRINE 3 | BRINE 4 | BRINE 5 |
|---|---|---|---|---|---|---|
| 2 | B | soluble | soluble | soluble | soluble | dispersible |
| 3 | C | dispersible | soluble | soluble | soluble | dispersible |
| 4 | D | soluble | soluble | soluble | soluble | soluble |
| 5 | E | insoluble | soluble | insoluble | insoluble | insoluble |
| 6 | C + E | insoluble | soluble | insoluble | insoluble | insoluble |
| 7 | D + E | insoluble | soluble | insoluble | insoluble | insoluble |

Table III shows the unexpected result that the various surfactants where the sulfonate and ether carboxylate are on the same molecule are soluble in all the brines tested whereas in many cases the individual sulfonates (E) and mixtures of the sulfonates and alcohol ether carboxylates (C+E and D+E) are not.

Tables IV and V shows the interfacial tension (IFT) in millineutons/meter (mN/m) against a crude oil having 27 API Gravity at 95° C. for 0.10 wt % surfactant. All IFTs were obtained using a University of Texas Model 500 spinning drop interfacial tensiometer after spinning at 95° C. for 1 hour. The data shows low IFT can be obtained with low surfactant concentration when the amount of ethylene oxide averages 3.8 to 6.8 Moles/Mole of oleyl alcohol.

TABLE IV

IFT Properties

| TEST | SURFAC-TANT | BRINE 1 | BRINE 2 | BRINE 3 | BRINE 4 | BRINE 5 |
|---|---|---|---|---|---|---|
| 1 | A | 0.891 | 0.005 | 0.012 | insoluble | insoluble |
| 2 | B | 0.356 | 0.009 | 0.003 | 0.003 | 0.002 |
| 3 | C | 0.769 | 0.070 | 0.090 | 0.122 | 0.256 |
| 4 | D | 0.066 | 0.031 | 0.022 | 0.020 | 0.020 |
| 5 | E | insoluble | 0.007 | insoluble | insoluble | insoluble |
| 6 | C + E | insoluble | 0.005 | insoluble | insoluble | insoluble |
| 7 | D + E | insoluble | 0.009 | insoluble | insoluble | insoluble |

Table V also shows that in this case the individual surfactants A and B containing 2 and 9 moles of ethylene oxide respectively do not give ultra-low IFTs with brine 1; however blends containing various amounts of the two do give IFTs below $10^{-2}$ mN/m.

TABLE V

Comparison of IFTs with Various Surfactant Mixtures

| A wt % | B wt % | Avg Mole EO | BRINE 1 |
|---|---|---|---|
| 100 | 0 | 2.0 | 0.891 |
| 75 | 25 | 3.8 | 0.0080 |
| 50 | 50 | 5.5 | 0.0058 |
| 25 | 75 | 6.8 | 0.0023 |
| 0 | 100 | 9.0 | 0.356 |

Table VI shows the IFTs obtained using individual surfactants defined by structure I where the moles of EO are have been varied from 2 to 9. This shows that the single surfactant system can give the same IFT values as the blends from Table IV with the additional advantage of having no possibility of chromatographic separation since they are single component systems.

TABLE VI

IFT for Various Single Component Systems

| Mole EO | BRINE 1 |
|---|---|
| 2.0 | 0.891 |
| 4.0 | 0.0080 |
| 6.0 | 0.0051 |
| 7.0 | 0.0035 |
| 8.0 | 0.093 |
| 9.0 | 0.356 |

Table VII compares the adsorption of the composition of this invention surfactant B with a 1:1 molar mixture of surfactant D and surfactant E to show the effectiveness of having both the sulfonate and ether carboxylate on one molecule. 0.2 wt % surfactant D and 0.2 wt % surfactant E alone were also included to correct for the amount of each of these surfactants adsorbed. All tests were done using 0.20 wt % total surfactant in Brine 2. The static adsorption was run by mixing 50.0 grams of surfactant solution with 10.0 grams of 200 mesh beach sand on a wrist action shaker for 16 hours and then determining the amount of surfactant remaining compared to the original amount added. Table VII shows the amount adsorbed in mg surfactant/gram sand.

TABLE VII

Adsorption Tests

| | Original wt, g | Amount remaining | Adsorbed | mg/g | % adsorbed |
|---|---|---|---|---|---|
| Surfactant B | 0.100 | 0.096 | 0.014 | 1.4 | 14 |
| Surfactant D + E | 0.100 | 0.039 | 0.061 | 6.1 | 61 |
| Surfactant D | 0.100 | 0.022 | 0.078 | 7.8 | 78 |
| Surfactant E | 0.100 | 0.045 | 0.055 | 5.5 | 55 |

The data from Table VII shows that the alcohol ether carboxylate (surfactant D) is strongly adsorbed (78%) onto the sand. The sulfonate (surfactant E) is not adsorbed as much however this product is not compatible with brines having salt concentrations of 5 wt % or more as shown in Table III. The mixing of surfactant E and surfactant D indicates that the adsorption of surfactant D is very large and not reduced by mixing with surfactant E, However, the adsorption of the composition of this invention surfactant B is very low. This indicates that an unexpected synergistic effect occurs when the alcohol ether carboxylate and the sulfonate are combined on the same molecule.

While the invention has been described in connection with a preferred embodiment, it is not intended to limit the scope of the invention to the particular form set forth, but on the contrary, it is intended to cover such alternatives, modifications, and equivalents as may be included within the spirit and scope of the invention as defined by the appended claims.

What is claimed is:

1. A composition of matter of having both a sulfonate and an ether carboxylate functionality group on the same aromatic molecule with the structure

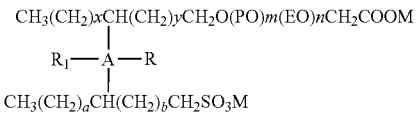

where m+n=1-30 or more,
x+y=0-28,
EO=oxirane
PO=methyl oxirane

M=H, Na, K, NH$_3$, Amine, Ca, Mg,

R and R$_1$ are each separately and independently H, branched or linear alkyl, branched or linear alkenyl, A=aromatic, and, a+b=0 to 30.

2. The compositions described in claim 1 where the aromatic ring is chosen from the group benzene, toluene, o-xylene, m-xylene, p-xylene, phenol, naphthalene, phenyl ether.

\* \* \* \* \*